(12) United States Patent
Chen et al.

(10) Patent No.: US 9,126,056 B2
(45) Date of Patent: Sep. 8, 2015

(54) METHOD OF PROMOTING HAIR GROWTH

(75) Inventors: Han-Min Chen, Taipei (TW); Li-Te Chin, Taipei (TW)

(73) Assignee: ENERGENESIS BIOMEDICAL CO., LTD., New Taipei (TW)

( * ) Notice: Subject to any disclaimer, the term of this patent is extended or adjusted under 35 U.S.C. 154(b) by 171 days.

(21) Appl. No.: 12/766,927

(22) Filed: Apr. 26, 2010

(65) Prior Publication Data

US 2011/0263618 A1 Oct. 27, 2011

(51) Int. Cl.
- *A61Q 7/00* (2006.01)
- *A61K 31/52* (2006.01)
- *A61K 8/49* (2006.01)
- *A61Q 5/02* (2006.01)
- *A61Q 5/12* (2006.01)

(52) U.S. Cl.
CPC .............. *A61Q 7/00* (2013.01); *A61K 8/4953* (2013.01); *A61K 31/52* (2013.01); *A61Q 5/02* (2013.01); *A61Q 5/12* (2013.01)

(58) Field of Classification Search
None
See application file for complete search history.

(56) References Cited

U.S. PATENT DOCUMENTS 5,656,264 A * 8/1997 Hanada et al. ................ 424/70.1
2005/0000040 A1 * 1/2005 Berens et al. ...................... 8/406

FOREIGN PATENT DOCUMENTS

JP 03133920 A * 6/1991 ............... A61K 7/06
WO WO 2009027112 A1 * 3/2009

OTHER PUBLICATIONS

"Hair loss and eyebrow and eyelash loss" by Rockoff, available at http://www.medhelp.org (Jan. 2007).*
"Pharmaceutical Salts" by Berge et al., J. Pharm. Sci. 66,1-19 (1977).*
"Adenosine increases anagen hair growth and thick hairs in Japanese women with female pattern hair loss: A pilot, double-blind, randomized, placebo-controlled trial" by Oura et al., J. Dermatol. 35, 763-67 (2008).*
Machine Translation of WO 2009/027112 (Sep. 2014).*
"Androgens and the Hair Follicle: Cultured Human Dermal Papilla Cells as a Model System" by Randall et al., Ann. N.Y. Acad. Sci. 642, 355-75 (1991).*

* cited by examiner

*Primary Examiner* — Theodore R West
(74) *Attorney, Agent, or Firm* — Muncy, Geissler, Olds & Lowe, P.C.

(57) ABSTRACT

The present invention is an invention belonging to the life style improving cosmetic in the field of hair maintenance and enrichment. More particularly, it relates to cosmetic compositions having an improved hair care actions such as to prevent hair loss and/or to promote hair growth on the scalp and skin of a mammal.

10 Claims, 1 Drawing Sheet

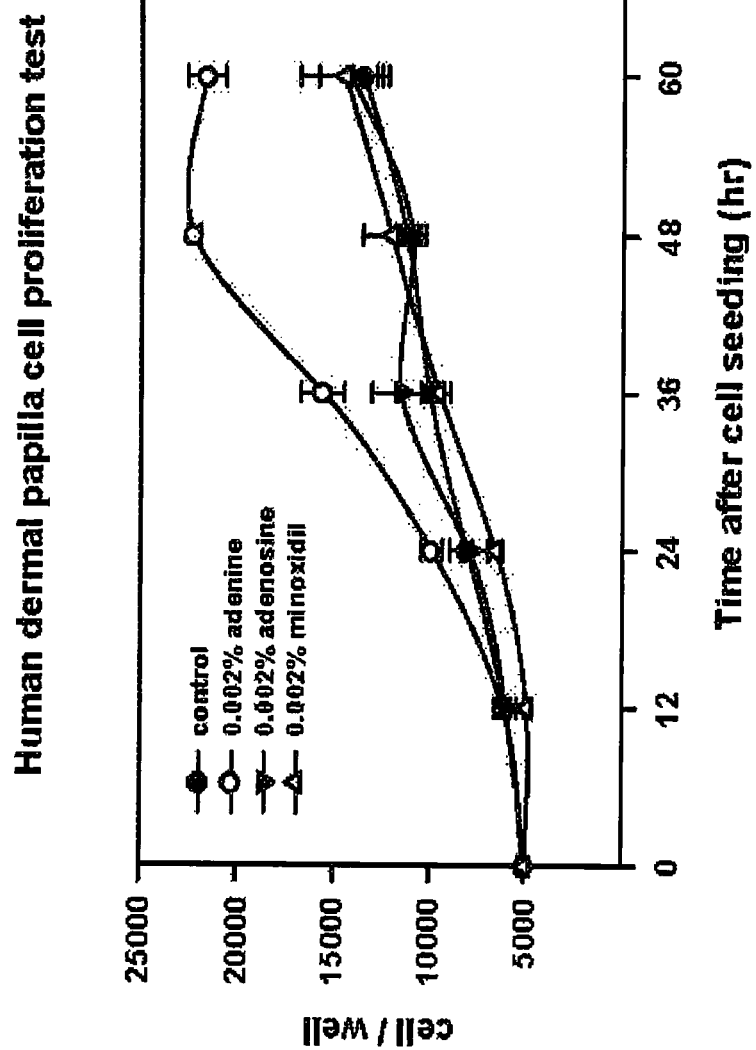

METHOD OF PROMOTING HAIR GROWTH

BACKGROUND OF THE INVENTION

1. Technical Field

The present invention is an invention belonging to the life style improving cosmetic in the field of hair maintenance and enrichment. More particularly, it relates to cosmetic compositions having an improved hair care actions such as to prevent hair loss and/or to promote hair growth on the scalp and skin of a mammal.

2. Description of the Related Art

As the aged population is increasing and stress is high in modern society, there are a growing number of people under the threat of hair fall and hair loss. Although medically benign, they can cause tremendous emotional and psychosocial pressure in affected patients and their families. The vast majority of people are thus trying to avoid baldness or alopecia like the plaque, thus an effective treatment is urgently needed.

The Hair Growth Cycle

In mammals, hair does not continuously grow but undergoes a cycle of activity involving alternate periods of growth and rest. Three stages in the hair growth cycle are as follows, (i) Anagen: an active stage, during which the hair follicle penetrates deep into the dermis with the cells of the bulb dividing rapidly and differentiating to form the hair, (ii) Catagen: a regressive stage, during which the follicle regresses upwards through the dermis and hair growth ceases, (iii) Telogen: a resting stage, in which the regressed follicle contains a small secondary germ with an underlying ball of tightly packed dermal papilla cells.

The initiation of a new anagen stage is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

It is generally considered that hair loss is elicited by male hormones, dihydrotesterone (DHT), produced in the hair follicles. DHT may decrease the flow of blood to the hair papilla and hair follicles. It may also cause hypersteatosis, abnormalities on the scalp due to production of reactive oxygen species and/or poor nutrition, etc. Conventional hair tonic compositions have thus been formulated with ingredients having actions in eliminating or alleviating these causes. For example, in order to improve the circulation of blood at the scalp, vasodilators such as swertia herb extract, vitamin E and its derivatives, acetylcholine derivatives, and skin function promoters such as cepharanthine were formulated. Antipyrotics such as shikon extract were also formulated to suppress inflammation of the scalp. Furthermore, to enrich the hair follicles etc., amino acids such as serine and methione, vitamins such as vitamin B 6, etc. are formulated. These are used for the purpose of the prevention of hair loss, the promotion of hair growth, etc.

Two medical treatments were approved by the U.S. Food and Drug Administration (FDA) for male baldness, finasteride (Johannsson, U.S. Pat. No. 2006/0099251 A1) and minoxidil (Chidsey, U.S. Pat. No. 4,139,619). Finasteride was originally used for the treatment of benigh prostatic hyperplasia (BPH) and subsequently found effective for the treatment of male pattern baldness. Finasteride works by inhibiting the activity of 5-alpha-reductase, the enzyme responsible for the conversion of free testosterone to DHT that may induce the follicular miniaturization (Dallob et al, 1994). Finasteride was now marketed as the brand-name drugs, Propecia, by Merck for the baldness treatment on men but not women. Minoxidil is a vasodilator and was originally used as an oral drug (Loniten) to treat high blood pressure. It was discovered to have the side effect of hair growth and reversing baldness in the 1980s. Upjohn Corporation received FDA approval to market a topical solution that contained 2% minoxidil to be used to treat baldness and hair loss (Rogaine and Regaine). The acting mechanism for minoxidil is unclear, but many speculate that by widening blood vessels, opening potassium channels, and allowing more oxygen, blood and nutrients to the follicle.

Minoxidil-induced hair growth was also suggested mediated by adenosine (Li et al, 2001), and presumably through the A2b adenosine receptor pathways (Iino et al, 2007). Therefore, adenosine was unveiled as another functional treatment of baldness Nevertheless; there is general concern that systemic side-effects that may be derived, particularly following topical application of minoxidil and adenosine. Thus it is generally recognized in the medical literature that the side effects of orally administered minoxidil are very serious, and include fluid retention, tachycardia, dyspnea, gynecomastia, fatigue, nausea and cardiotoxicity. There is also evidence that certain side effects have been experienced following topical application of minoxidil. On the other hand, there is a close association of adenosine in cancer formation. The A(1), A(2A), A(2B) and A(3) G-protein-coupled cell surface adenosine receptors (ARs) are found to be upregulated in various tumor cells and activation of the receptors might promote tumor growth via a range of signaling pathways (Fishman et al, 2009).

While various attempts have been made as explained above, current hair tonics have not necessarily had sufficient hair care actions such as prevention of hair loss and promotion of hair growth in any area of the scalps. For examples, finasteride and minoxidil treatments claimed to work on both the vertex area and the frontal area, but are most successful in only the vertex area. In addition, most baldness treatment takes a long period, such as four to six months, before apparently showing the treatment effect. Possibly, the only means which has met with partial success for growing hair on the bald or balding human head is by transplantation of hair to the bald areas. This is usually a painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Current baldness treatments may lift the gloom, but the wide-spread dissatisfactions indicate they are not enough to propel the hair of a relatively regressive and/or resting status toward an active stage, probably due to the diversity of reasons for hair loss and the complexity of the mechanism of hair growth.

It is therefore desirable to provide a novel hair tonic composition having efficient hair care actions on the most areas of scalps.

SUMMARY OF THE INVENTION

The objects of the present invention are to solve the problems in the prior art and to provide a novel and effective hair tonic composition having superior hair care actions. In accordance with the present invention, there is provided a hair tonic composition comprising, at least one active ingredient selected from the group consisting of adenine or salts of adenine thereof.

BRIEF DESCRIPTION OF THE DRAWINGS

FIG. 1, is a graph showing the results of the promotion of dermal papilla cell proliferation by adenine.

DESCRIPTION OF THE PREFERRED EMBODIMENTS

The present inventors engaged in broad studies on various substances to solve the problem and found that adenine or salts of adenine have superior hair care actions such as hair loss preventing action and hair growth promoting action, whereby the present invention has been completed.

That is, the present invention provides a hair tonic composition containing adenine or salts of adenine as an active ingredient. The adenine capable of formulating, as an active ingredient, in the hair tonic composition of the present invention is one type of purine. Further, in the salt of adenine, as the counter ion for forming the salt, any substance may be used so long as forming acid and counter ions. For example, chloride, acetate and sulfate, etc. may be mentioned. Further, it is also possible to use the hydrate as the salt of adenine In the hair tonic composition of the present invention, it is possible to use, adenine or salts of adenine, those which are commercially available as reagents. The content of the adenine and/or salts of adenine in the hair tonic composition of the present invention can be varied depending upon the form, method of application, etc. of the hair tonic composition of the present invention, preferably 0.001 to 0.1% by weight. If the content is less than 0.001% by weight of the total weight of the hair tonic composition, the desired effect of the present invention does not tend to be sufficiently obtained, and therefore, this is not preferable, while if the amount is more than 0.1% by weight, there is a remarkable tendency of causing problems in the preparation, and therefore is again not preferred.

The type of preparation which the hair tonic composition of the present invention may take is not particularly limited so long as it is a type of preparation which can be applied to the skin, in particular, the scalp. For example, a liquid, emulsion, ointment, etc. may be used. Further, the hair tonic composition of the present invention may be of any form such as a hair tonic, hair clear lotion, hair care conditioner, hair care gel, hair care mousse and shampoo, etc.

The compositions of the invention comprise a cosmetically acceptable vehicle to act as a diluant, dispersant or vehicle for adenine, so as to facilitate its distribution when the composition is applied to the skin. Vehicles other than or in addition to water can include liquid or solid emollients, solvents, humectants, thickeners and powders.

Cosmetically Acceptable Vehicles

The cosmetically acceptable vehicle will usually form from 1% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well-known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition.

When the compositions of the invention are formulated as an oily solution or gel, the fatty phase may constitute more than 90% of the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase, into the aqueous phase.

Exemplary oils which may be used according to this invention include plant oils (coconut oil, liquid fraction of karite butter or sunflower oil), mineral oils (liquid petrolatum), animal oils (perhydrosqualene), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylatelalkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The hair tonic composition of the present invention may be administered transdermally through direct coating or spraying on the skin. Further, the dosage of the hair tonic composition of the present invention differs depending on age, personal differences, states of the disease, form of the hair tonic composition, etc. and cannot be clearly specified, but when administered to humans, the dosage is one by which adenine or salts of adenine are given in an amount of generally 0.0001 to 10.0 mg, preferably 0.001 to 0.1 mg, per kilogram body weight per day. This amount is preferably administered once a day or divided into two to four applications a day.

The hair tonic composition of the present invention has both a superior hair loss preventing action and hair growth promoting action and hair care action in humans and other mammals and is useful as a pharmaceutical, quasi-pharmaceutical, or cosmetic composition for hair care.

EXAMPLES

The present invention will now be explained in further detail with reference to, but is not limited to, the following Examples. In the following Examples, the "%" means % by weight, unless otherwise noted.

First, formulations of the hair tonic composition of the present invention will be given as the following four examples.

Example 1-4

Preparation of Hair Tonic

| INGREDIENT | Example 1 | Example 2 | Example 3 % (w/w) | Example 4 | Control |
|---|---|---|---|---|---|
| Adenine sulfate | 0 | 0.0001-0.0005 | 0.001-0.002 | 0.002-0.01 | 0 |
| Folinic acid | 0.0005 | 0.0005 | 0.0001 | 0.0001 | 0.0001 |
| Menthol | 0.1 | 0.1 | 0.1 | 0.05 | 0.05 |
| Benzoyl peroxide | 0.05 | 0.05 | 0.05 | 0.01 | 0.01 |
| PEG-40 hydrogenated castor oil | 1.0 | 1. | 0.5 | 0.5 | 1.0 |
| Ethanol | 5.0 | 10.0 | 5.0. | 10.0 | 5.0 |
| Ion exchanged water | balance | balance | balance | balance | balance |

Manufacturing Procedure:
(1) Adenine sulfate was mixed and stirred with folinic acid, menthol, benzoyl peroxide, PEG-40 hydrogenated castor oil, ethanol and a part of the ion exchanged water to obtain a solution.
(2) The remainder of the ion exchanged water was then added to the solution to obtain the hair tonic.

Next, the hair growth promoting action of hair tonic Example 1 to 4 obtained above was evaluated. Further, the hair care action of hair tonic Example 3 and 4 obtained above was evaluated.

Hair Growth Promoting Action Test Using Animals.

Balb/c mice in the resting stage of the hair cycle were used. That is, six groups of 10 mice each were prepared. The hair was shaved off from the back of the mice by shears and shavers, then hair tonic Example 1 to 4 or the Control were coated on the shaved portions of the mice in the groups once a day in amounts of 0.2 ml a time. The area of re-growth of hair was measured after 14 and 28 days. The results are shown in Table 1 where numerical values are mean values.

TABLE 1

| | Example 1 | Example 2 | Example 3 | Example 4 | Control |
|---|---|---|---|---|---|
| | Area of hair sample re-growth (%) | | | | |
| After 14 days | 5 | 18 | 38 | 65 | 2 |
| After 28 days | 33 | 42 | 82 | 98 | 21 |

As clear from Table 1, the hair tonic composition (hair tonic Example 2, 3 and 4) of the present invention exhibits a significant effect in the hair growth promoting action test on mice. It was found that the hair tonic composition of the present, invention has a superior hair growth promoting action.

Hair Care Action Test

The hair care action, including the hair loss preventing action and the hair growth promoting action, of the hair tonic composition of the present invention was investigated on human subjects by the following method. The test samples were the hair tonic Example 3 and 4, and the Control. That is, the hair tonic Example 3 and 4 and the control were each coated on the scalps of totally 60 male test subjects with the baldness problem twice a day in 1 ml amounts each time for four months straight. The hair care action was evaluated by the assessment of hair characteristics following treatment using questionnaire. The investigating results are summarized in Table 2.

TABLE 2

| Change of hair appearance | Week 8 | | | Week 16 | | |
|---|---|---|---|---|---|---|
| | Example 3 (n = 25) | Example 4 (n = 28) | Control (n = 17) | Hair tonic 3 (n = 25) | Hair tonic 4 (n = 28) | Control (n = 17) |
| | Individuals (%, percentages in the tested group) | | | | | |
| +2 (improvement) | 4 (16%) | 5 (18%) | 0 (0%) | 9 (36%) | 13 (47%) | 0 (0%) |
| +1 (slight improvement) | 7 (28%) | 13 (46%) | 2 (12%) | 10 (40%) | 9 (32%) | 1 (6%) |
| 0 (no change) | 14 (56%) | 10 (36%) | 8 (47%) | 6 (24%) | 6 (21%) | 8 (47%) |
| −1 (slight decline) | 0 (0%) | 0 (0%) | 5 (29%) | 0 (0%) | 0 (0%) | 5 (29%) |
| −2 (decline) | 0 (0%) | 0 (0%) | 2 (12%) | 0 (0%) | 0 (0%) | 3 (18%) |
| Average scoring | 0.60 | 0.82 | −0.41 | 1.12 | 1.25 | −0.59 |

From the results of Table 3, it became clear that hair tonic composition of the present invention containing adenine or salts of adenine exhibits significant hair care action in human tests.

Further, since a hair growth promoting action was observed even in the hair tonic composition of the present invention containing adenine (hair tonic Example 3 and 4), it was clear that a similar hair care action is observed even in the hair tonic of the present invention containing adenine.

Example 5

Preparation of Hair Clear Lotion

| INGREDIENT | % (w/w) |
|---|---|
| Phase I | |
| PEG-40 Hydrogenated Castor Oil | 0.5 |
| Tween-20 (Polysorbate 20) | 0.2 |
| Octoxynol 10 (Triton X-100) | 0.1 |
| Phase II | |
| Adenine sulfate | 0.02 |
| Folinic acid | 0.01 |
| Menthol | 0.1 |
| Benzoyl peroxide | 0.1 |
| Fragrance | 0.2 |
| Ion exchanged water | 98.8 |

Manufacturing Procedure:

(1) Mix well all the components in Phase I and Phase II individually.

(2) Mix the solutions from above to obtain a hair clear lotion.

Example 6

Preparation of Hair Shampoo

| INGREDIENT | % (w/w) |
|---|---|
| Hydroxycellulose | 1.0 |
| Disodium EDTA | 0.1 |
| Sodium citrate | 0.2 |
| Polyquaternium 7 | 2 |

-continued

| INGREDIENT | % (w/w) |
|---|---|
| Sodium laurosyl sarcosinate | 10 |
| lauric acid amidopropylbetaine | 8 |
| Cocamidopropylamine oxide | 6 |
| Lauramide MEA | 6.2 |
| Urea | 0.3 |
| Propyl paraben | 0.2 |
| Adenine sulfate | 0.05 |
| Menthol | 0.1 |
| Benzoyl peroxide | 0.1 |
| Fragrance | 0.2 |
| Ion exchanged water | 65.55 |

Manufacturing Procedure:

(1) Disperse the hydroxycellulose in ion exchanged water by a mixer.

(2) Heat the above solution to 70° C. then add disodium EDTA and sodium citrate until dissolution is complete.

(3) Add Polyquaternium 7 to the above solution until dissolution is complete.

(4) Cool the above solution to 40° C. Add sodium laurosyl sarcosinate, lauric acid amidopropylbetaine, cocamidopropylamine oxide and lauramide MEA and mix well.

(5) Add urea, propyl paraben, adenine sulfate, menthol, benzoyl peroxide and fragrance to obtain the hair shampoo.

Example 7

Preparation of Hair Care Conditioner

| INGREDIENT | % (w/w) |
| --- | --- |
| Polyquaternium 7 | 3.0 |
| Guar hydroxypropyltrimonium chloride | 0.3 |
| Dimethicone copolyol | 1.0 |
| Adenine sulfate | 0.02 |
| Folinic acid | 0.01 |
| Fragrance | 0.5 |
| Ion exchanged water | 95.2 |

Manufacturing Procedure:

(1) Mix ion exchanged water and polyquaternium 7 well, then add guar hydroxypropyltrimonium chloride, dimethicone copolyol, adenine sulfate, folinic acid and fragrance to obtain a hair conditioner.

Examples 8 and 9

Preparation of Eyelash/Eyebrow Clear Lotion

| INGREDIENT | Example 8 % (w/w) | Example 9 | Control 2 |
| --- | --- | --- | --- |
| Phase I | | | |
| PEG-40 Hydrogenated Castor Oil | 0.5 | 0.5 | 0.5 |
| Tween-20 (Polysorbate 20) | 0.1 | 0.1 | 0.1 |
| Phase II | | | |
| Adenine sulfate | 0.1 | 0.05 | 0 |
| Folinic acid | 0.1 | 0.1 | 0.1 |
| Fragrance | 0.2 | 0.2 | 0.2 |
| Pyrogen free water | 99.0 | 99.05 | 99.1 |

Manufacturing Procedure:

(1) Mix well all the components in Phase I and Phase II individually.

(2) Mix the solutions from above to obtain a eyelash lotion

Eyelashes Growing Test

The eyelashes growing test, of the eyelash clear lotion composition of the present invention was investigated on human subjects by the following method. The test samples were Example 8, Example 9 and the Control 2.

That is, the eyelash clear lotion Example 8, Example 9 and the Control 2 were each coated using cotton swabs on the eyelashes of totally 48 female test subjects once a day in 0.5 ml amounts for three months straight. The eyelashes growing action was evaluated by using questionnaire, as well as measuring the average length of twenty eyelashes (millimeter). The investigating results are summarized in Table 3.

TABLE 3

| | After 2 month application | | |
| --- | --- | --- | --- |
| | Example 8 (n = 16) | Example 9 (n = 16) | Control 2 (n = 16) |
| +2 (improvement) | 2 (12.5%) | 4 (25%) | 0 (0%) |
| +1 (slight improvement) | 8 (50%) | 10 (67.5%) | 2 (12.5%) |
| 0 (no change) | 6 (37.5%) | 2 (12.5%) | 12 (75%) |
| −1 (slight decline) | 0 (0%) | 0 (0%) | 2 (12.5%) |
| −2 (decline) | 0 (0%) | 0 (0%) | 0 (0%) |
| Average scoring | 0.75 | 1.13 | 0.13 |
| Average length changing of eyelashes (mm) | 0.12 | 0.22 | 0 |

From the results of Table 3, it became clear that eyelash clear lotion composition of the present invention containing adenine or salts of adenine exhibits significant eyelashes growing action in human tests.

Eyebrow Growing Test

The eyebrow growing test, of the eyebrow clear lotion composition of the present invention was investigated on human subjects by the following method. The test samples were Example 8, Example 9 and the Control 2.

That is, the eyebrow clear lotion Example 8, Example 9 and the Control 2 were each coated using cotton swabs on the eyebrows of totally 60 test subjects once a day in 0.5 ml amounts for two months straight. The eyebrow growing action was evaluated by using questionnaire, as well as measuring the average length of ten eyebrows (millimeter). The investigating results are summarized in Table 4.

TABLE 4

| | After 2 month application | | |
| --- | --- | --- | --- |
| | Example 8 (n = 20) | Example 9 (n = 20) | Control 2 (n = 20) |
| +2 (improvement) | 4 (20%) | 3 (15%) | 0 (0%) |
| +1 (slight improvement) | 6 (30%) | 10 (50%) | 2 (10%) |
| 0 (no change) | 10 (50%) | 7 (35%) | 18 (90%) |
| −1 (slight decline) | 0 (0%) | 0 (0%) | 0 (0%) |
| −2 (decline) | 0 (0%) | 0 (0%) | 0 (0%) |
| Average scoring | 0.7 | 0.8 | 0.1 |
| Average length changing of eyelashes (mm) | 0.18 | 0.25 | 0 |

From the results of Table 4, it became clear that eyebrow clear lotion composition of the present invention containing adenine or salts of adenine exhibits significant eyebrow growing action in human tests.

Human Dermal Papilla Cell Proliferation Test

The promotion of cell proliferation by adenine was evaluated using human dermal papilla cells, compared with adenosine, and minoxidil under the following conditions, the results are shown in FIG. 1.

Determination of the proliferation of human dermal papilla cells in the culture media containing adenine, adenosine, and minoxidil. Supplements: 0.002% of adenine, adenosine, minoxidil.

Test Method:

(1) Prepare 0.002% adenine, adenosine, minoxidil containing testing media using the hair follicle dermal papilla cell media (cat. No. 611-500, Cell applications, Inc).

(2) Seed the isolated human dermal papilla cells in 96-well culture plate with a density of 5,000 cells per well. Add 0.1 mL prepared culture media into individual well.
(3) At 12, 24, 36, 48 and 60 hour after cell seeding, visually count the total cell number using hemacytometer.
(4) Evaluate the result.

From the results of FIG. 1, it became apparent that adenine promotes the proliferation of human dermal papilla cells. As explained above, according to the present invention, there is provided a hair tonic composition having superior hair care actions such as a hair loss preventing action and hair growth promoting action in humans and other mammals. While the present invention has been described with reference to the preferred embodiments, it understood that the embodiments are not intended to limit the scope of the present invention. The scope of the present invention is defined only by the appended claims.

What is claimed is:

1. A method of promoting hair growth in a human comprising selecting a person having hair loss or baldness and thereafter administering to said person in need thereof a composition consisting essentially of, as an active ingredient, an effective amount of adenine or a salt of adenine and a cosmetically acceptable vehicle thereof by applying said composition to scalp or hair roots of said person,
    wherein the amount of the active ingredient is 0.001% to 0.1% by weight, based upon the total weight of the composition.

2. The method of claim 1, wherein the vehicle is selected from the group consisting of liquid or solid emollients, solvents, humectants, thickeners and powders.

3. The method of claim 1, wherein the cosmetically acceptable vehicle is a hair tonic or hair clear lotion or hair care conditioner or hair care gel or hair care mousse or shampoo.

4. The method of claim 1, wherein a dosage of the adenine or a salt of adenine is 0.0001 to 10 mg/kg of body weight per day.

5. A method of promoting eyelash and eyebrow growth in a human comprising selecting a person having eyelash and eyebrow loss and administering to said person in need thereof a composition consisting essentially of as an active ingredient, an effective amount of adenine or a salt of adenine and a cosmetically acceptable vehicle thereof by applying said composition to eyelash and eyebrow of said person,
    wherein the amount of the active ingredient is 0.001% to 0.1% by weight, based upon the total weight of the composition.

6. The method of claim 5, wherein the cosmetically acceptable vehicle is a hair tonic or hair clear lotion or hair care conditioner or hair care gel or hair care mousse or shampoo.

7. The method of claim 5, wherein a dosage of the adenine or a salt of adenine is 0.0001 to 10 mg/kg of body weight per day.

8. A method of preventing hair fall in a human comprising selecting a person having hair loss or baldness and thereafter administering to said person in need thereof a composition consisting essentially of, as an active ingredient, an effective amount of adenine or a salt of adenine and a carrier thereof by applying said composition to scalp or hair roots of said person,
    wherein the amount of the active ingredient is 0.001% to 0.1% by weight, based upon the total weight of the composition.

9. The method of claim 8, wherein the carrier is a hair tonic or hair clear lotion or hair care conditioner or hair care gel or hair care mousse or shampoo.

10. The method of claim 8, wherein a dosage of the adenine or a salt of adenine is 0.0001 to 10 mg/kg of body weight per day.

* * * * *